US010111648B2

(12) United States Patent
Tegels et al.

(10) Patent No.: US 10,111,648 B2
(45) Date of Patent: Oct. 30, 2018

(54) PROCEDURAL SHEATH ADAPTER FOR VASCULAR CLOSURE DEVICE

(75) Inventors: Zachary J. Tegels, Minneapolis, MN (US); Philip J. Ebeling, Maple Grove, MN (US)

(73) Assignee: TERUMO PUERTO RICO, LLC, Caguas, PR (US)

( * ) Notice: Subject to any disclaimer, the term of this patent is extended or adjusted under 35 U.S.C. 154(b) by 182 days.

(21) Appl. No.: 14/116,713

(22) PCT Filed: May 17, 2012

(86) PCT No.: PCT/US2012/038370
§ 371 (c)(1),
(2), (4) Date: Jan. 13, 2014

(87) PCT Pub. No.: WO2012/158931
PCT Pub. Date: Nov. 22, 2012

(65) Prior Publication Data
US 2014/0135826 A1 May 15, 2014

Related U.S. Application Data

(60) Provisional application No. 61/488,097, filed on May 19, 2011.

(51) Int. Cl.
*A61B 17/04* (2006.01)
*A61B 17/00* (2006.01)
(52) U.S. Cl.
CPC .............. *A61B 17/0057* (2013.01);
*A61B 2017/00623* (2013.01); *A61B 2017/00659* (2013.01)

(58) Field of Classification Search
CPC ...... A61B 17/0057; A61B 2017/00623; A61B 2017/00659; Y10T 403/5713;
(Continued)

(56) References Cited

U.S. PATENT DOCUMENTS 5,021,059 A 6/1991 Kensey et al.
5,676,689 A 10/1997 Kensey et al.
(Continued)

FOREIGN PATENT DOCUMENTS

WO 9529635 A1 11/1995
WO 2006124245 A2 11/2006

OTHER PUBLICATIONS

PCT International Search Report for PCT International Patent Application No. PCT/US2012/038370, dated Oct. 8, 2012.
(Continued)

*Primary Examiner* — Diane Yabut
*Assistant Examiner* — Erich Herbermann
(74) *Attorney, Agent, or Firm* — Buchanan Ingersoll & Rooney PC

(57) ABSTRACT

A tissue puncture closure device includes an anchor, a sealing plug, a compaction member, a suture, a handle portion, a sheath attachment member, and a sheath adapter. The compaction member is configured to compress the sealing plug towards the anchor. The suture is coupled to the sealing plug and anchored. The handle portion is arranged proximal of the sealing plug and anchor. The sheath attachment member extends from the handle portion. The sheath adapter has a first end portion configured to mount to the sheath attachment member, and a second end portion configured to mount to a procedural sheath that is inserted into a tissue puncture.

4 Claims, 12 Drawing Sheets

(58) Field of Classification Search
CPC ......... Y10T 403/5706; Y10T 403/5733; Y10T 403/50; Y10T 403/57
USPC .......................................... 606/213–215, 232
See application file for complete search history.

(56) References Cited

U.S. PATENT DOCUMENTS

| | | | |
|---|---|---|---|
| 6,045,569 | A | 4/2000 | Kensey et al. |
| 6,090,130 | A | 7/2000 | Nash et al. |
| 7,250,057 | B2 | 7/2007 | Forsberg |
| 2005/0085851 | A1 | 4/2005 | Fiehler et al. |
| 2005/0125030 | A1 | 6/2005 | Forsberg et al. |
| 2006/0135991 | A1* | 6/2006 | Kawaura ............ A61B 17/0057 606/213 |
| 2006/0229674 | A1 | 10/2006 | Forsberg |
| 2006/0265006 | A1 | 11/2006 | White et al. |
| 2007/0025811 | A1* | 2/2007 | Wilhelm ................. F16L 37/34 403/300 |
| 2009/0256355 | A1* | 10/2009 | Wicks ................. A61M 39/105 285/319 |
| 2010/0106150 | A1* | 4/2010 | Thompson ......... A61B 18/1492 606/29 |
| 2011/0066181 | A1 | 3/2011 | Jenson et al. |
| 2011/0077598 | A1 | 3/2011 | Pipenhagen et al. |
| 2012/0284991 | A1* | 11/2012 | Kusz ..................... A61M 39/10 29/428 |

OTHER PUBLICATIONS

European Office Action dated May 8, 2017, by the European Patent Office in corresponding EP Application No. 16151452.6 (5 pgs).

* cited by examiner

PROCEDURAL SHEATH ADAPTER FOR VASCULAR CLOSURE DEVICE

RELATED APPLICATION

This claims the benefit of U.S. Provisional Application No. 61/488,097, filed May 19, 2011, which is hereby incorporated by reference herein in its entirety.

TECHNICAL FIELD

The present disclosure relates generally to medical devices and more particularly to adapters that interface between vascular closure devices and procedural sheaths.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties herein by this reference.

Typical closure devices such as the ones described in the above-mentioned patents are operable with an insertion sheath that has a specifically designed closure device interface and other features unique to a vascular closure procedure (i.e., a closure insertion sheath). The insertion sheath used with the intraluminal treatment instruments (i.e., a procedural sheath) is typically exchanged with the closure insertion sheath after completion of the intraluminal treatment and before closure of the puncture. Sheath exchanges can be time consuming and may result in complications for the patient and operator. There is a need for improved insertion sheaths and methods that limit the need for sheath exchanges related to a tissue puncture closure such as a vascular closure.

SUMMARY

One aspect of the present disclosure is directed to a tissue puncture closure device that includes an anchor, a sealing plug, a compaction member, a suture, a handle portion, a sheath attachment member, and a sheath adapter. The compaction member is configured to compress the sealing plug towards the anchor. The suture is coupled to the sealing plug and anchor. The handle portion is arranged proximal of the sealing plug and anchor. The sheath attachment member extends from the handle portion. The sheath adapter has a first end portion configured to mount to the sheath attachment member, and a second end portion configured to mount to a procedural sheath that is inserted into a tissue puncture. The sheath adapter may include a sheath connection portion positioned at the second end portion and a closure device connection portion positioned at the first end portion. The closure device connection portion may define at least one aperture sized to receive the sheath attachment member. The closure device connection portion may define first and second apertures sized to receive first and second portions of the sheath attachment member. The sheath connection portion may include at least one latch member configured to extend into a recess of the procedural sheath. Alternatively, the sheath connection portion may be configured to provide an interference fit with an outer surface of the procedural sheath. In further examples, the sheath connection portion may be configured to contact an inner surface of the procedural sheath.

Another aspect of the present disclosure is directed to a sheath adapter that is configured for use between a tissue puncture closure device and a procedural sheath. A procedural sheath is adapted for insertion into a tissue puncture, and the tissue puncture closure device is adapted for partial insertion into the procedural sheath and sealing of the tissue puncture. The sheath adapter may include a sheath connection portion, a closure device connection portion, and an aperture. The sheath connection portion is positioned at a distal end of the sheath adapter. The closure device connection portion is positioned at a proximal end of the sheath adapter. The aperture is sized for passage of a carrier tube of the tissue puncture closure device through the sheath adapter.

The sheath connection portion of the adapter may include at least one latch member configured to extend into a recess of the procedural sheath. The sheath connection portion may alternatively be configured to provide an interference fit with an outer surface of the procedural sheath. The closure device connection portion may define at least one connection aperture sized to receive a sheath connection member of the tissue puncture closure device. In another example, the sheath connection portion is configured to releasably mount to a proximal end portion of the procedural sheath, and the closure device connection portion is configured to releasably mount to a sheath connection member of a tissue puncture closure device. The sheath adapter may have a length extending from the distal end to the proximal end of the sheath adapter, wherein the length is adjustable to accommodate sheaths of different length.

A further aspect of the present disclosure is directed to a method of sealing a tissue puncture. The method includes providing a procedural sheath, a sheath adapter, and a tissue puncture closure device. The tissue puncture closure device includes an anchor, a sealing plug, a suture coupled to the anchor and sealing plug, and a compaction member. The method may further include inserting a distal end portion of the procedural sheath into a tissue puncture, mounting the sheath adapter to a proximal end portion of the procedural sheath, and mounting the tissue puncture closure device to the sheath adapter.

Mounting the tissue puncture closure device to the sheath adapter may include inserting an anchor and sealing plug of the tissue puncture closure device through the adapter. Mounting the tissue puncture closure device to the sheath adapter may also include inserting at least one closure device connection member of the tissue puncture closure device into a closure device connection aperture of the sheath adapter. Mounting the tissue puncture closure device to the sheath adapter may occur after mounting the sheath adapter to the procedural sheath. Mounting the sheath adapter to a proximal end of the procedural sheath may include providing a snap-fit connection between a hub portion of the procedural sheath and a sheath connection member of the sheath adapter.

Mounting the sheath adapter to a proximal end of the procedural sheath may include connecting the sheath adapter to a flushing port of the procedural sheath. Mounting the sheath adapter to a proximal end of the procedural sheath may include providing an interference fit between the sheath adapter and the procedural sheath. The sheath adapter may be releasably mounted to the procedural sheath, and the tissue puncture closure device may be releasably mounted to the sheath adapter. Mounting the tissue puncture closure device to the sheath adapter may occur after positioning the anchor in a vessel that defines the tissue puncture.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not intended to be limiting.

Throughout the drawings, identical reference numbers designate similar, but not necessarily identical, elements.

DETAILED DESCRIPTION

Figure 1:
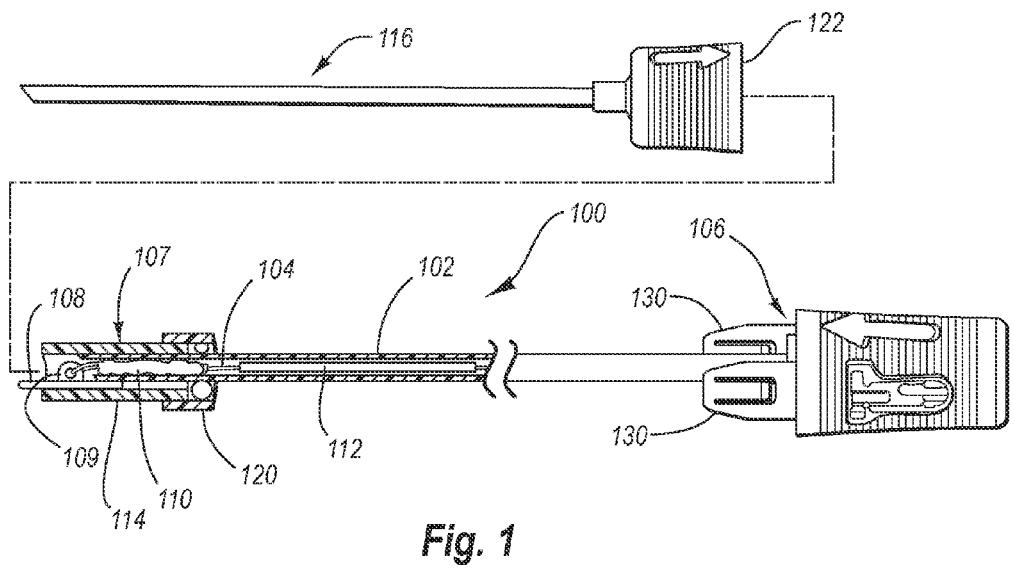
FIG. 1 is an exploded side view of an example vascular closure assembly according to the present disclosure.

As mentioned above, vascular procedures are conducted throughout the world and require access to a vessel (e.g., an artery) through a puncture. Most often, the vessel is a femoral artery. A procedural insertion sheath may be used to provide access into the artery through the puncture for instruments and devices used to treat the patient or conduct diagnostics. Such instruments and devices may include, for example, catheters or guide wires that pass through a lumen defined by the procedural insertion sheath. The procedural sheath is often exchanged with a different insertion sheath that is suited for use with the particular vascular closure device used to close the puncture after the treatment or diagnostics are completed. Exchanging the procedural sheath can be time consuming and may result in complications for the patient.

The present disclosure is directed to systems, devices and methods that eliminate the need for a sheath exchange prior to conducting a vascular closure procedure. An example vascular closure assembly of the present disclosure includes an adapter for use between the vascular closure device and the insertion sheath. The adapter includes a closure device interface that provides a connection to the vascular closure device. The adapter also includes a sheath interface that provides a connection to the insertion sheath. Different adapters may be used with various insertion sheath configurations wherein each adapter has the same closure device interface for use with a given vascular closure device. Similarly, different adapters may be used with various vascular closure device configurations and the same insertion sheath configuration. Many different insertion sheath interface constructions may be used with the adapter, including, for example, a snap-fit construction for engagement with an inner or outer surface of the insertion sheath, an interference fit construction, a snap-ring construction, a barb construction, or a combination of two or more of these example interface constructions.

Typically, the adapter is connected to a hub of the insertion sheath. The adapter is usually connected to the insertion sheath prior to connecting the adapter to the vascular closure device. In at least some arrangements, the adapter is releasably mounted to the insertion sheath. Portions of the vascular closure device such as the carrier tube and compaction member may have an extended length to account for the use of the adapter between the insertion sheath and the vascular closure device.

As used in this specification and the appended claims, the terms "compact," "compaction," and "compacting" are used broadly to mean packing down and compressing by one or a succession of blows or taps or smooth, steady pressure, but not by excessive force. The terms "tamp" and "tamping" may relate to certain types or forms of "compaction" and "compacting." "Engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-4, a vascular closure device 100 is shown according to the prior art. Some example closure devices are disclosed in U.S. Published Patent Application Nos. 2005/0085851, 2006/0265006 and 2006/0229674, which applications are incorporated in their entirety herein by reference. The vascular closure device 100 includes a carrier tube 102 with a filament or suture 104 extending at least partially therethrough. The closure device 100 also includes a first or proximal end 106 and a second or distal end 107. External to the distal end 107 of the carrier tube 102 is an anchor 108. The anchor may include an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may comprise, for example, randomly oriented fibrous material bound together by chemical means. The collagen pad 110 is slidingly attached to the suture 104 as the suture passes distally through the carrier tube 102. As the suture traverses the anchor 108 and reenters the carrier tube 102, the suture 104 is securely slip knotted proximal to the collagen pad 110 to facilitate cinching of the collagen pad 110 when the closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 using a bypass tube 114 that is disposed over the distal end 107 of the carrier tube 102.

Figure 2:
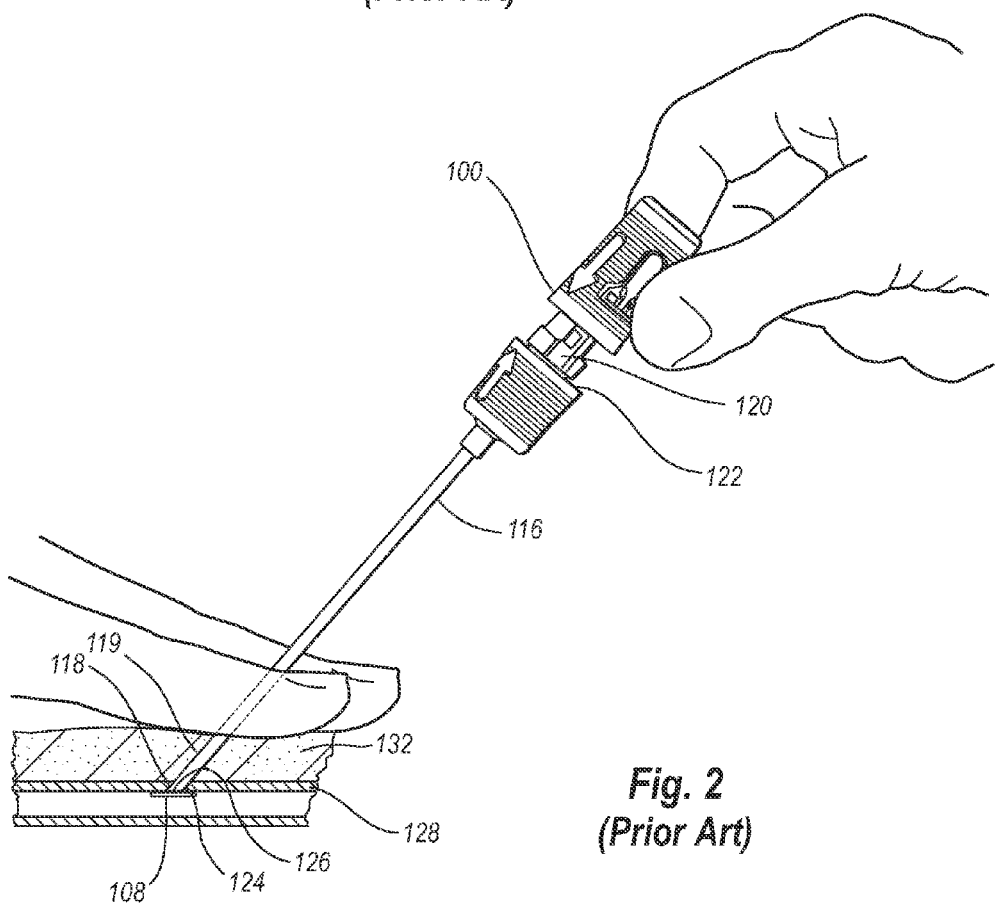
FIG. 2 is a side view of the vascular closure assembly of FIG. 1 assembled with a portion thereof inserted into a vascular puncture.
Figure 3:
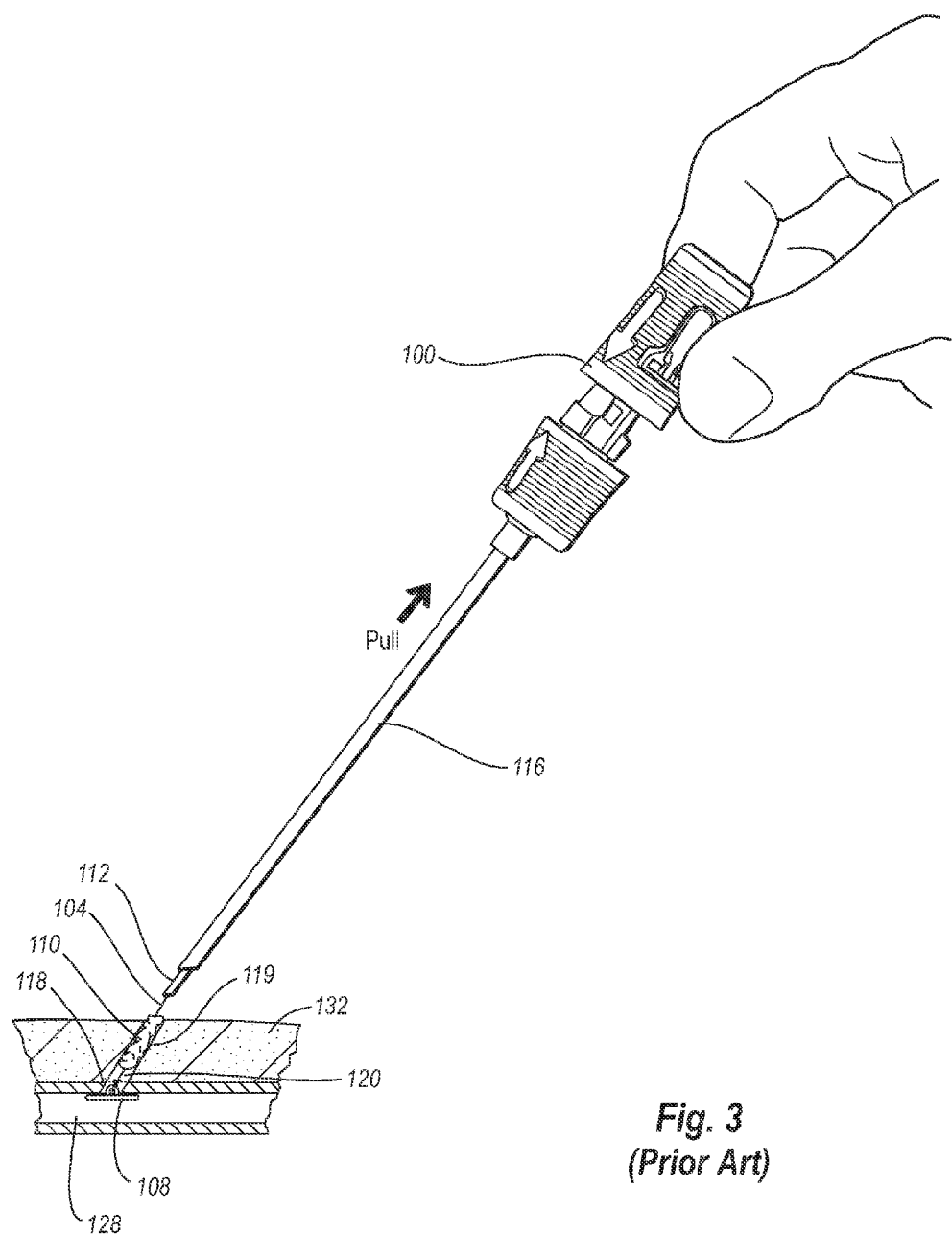
FIG. 3 is a side view of the vascular closure assembly of FIG. 1 with a sealing pad ejected adjacent to the vascular puncture.
Figure 4:
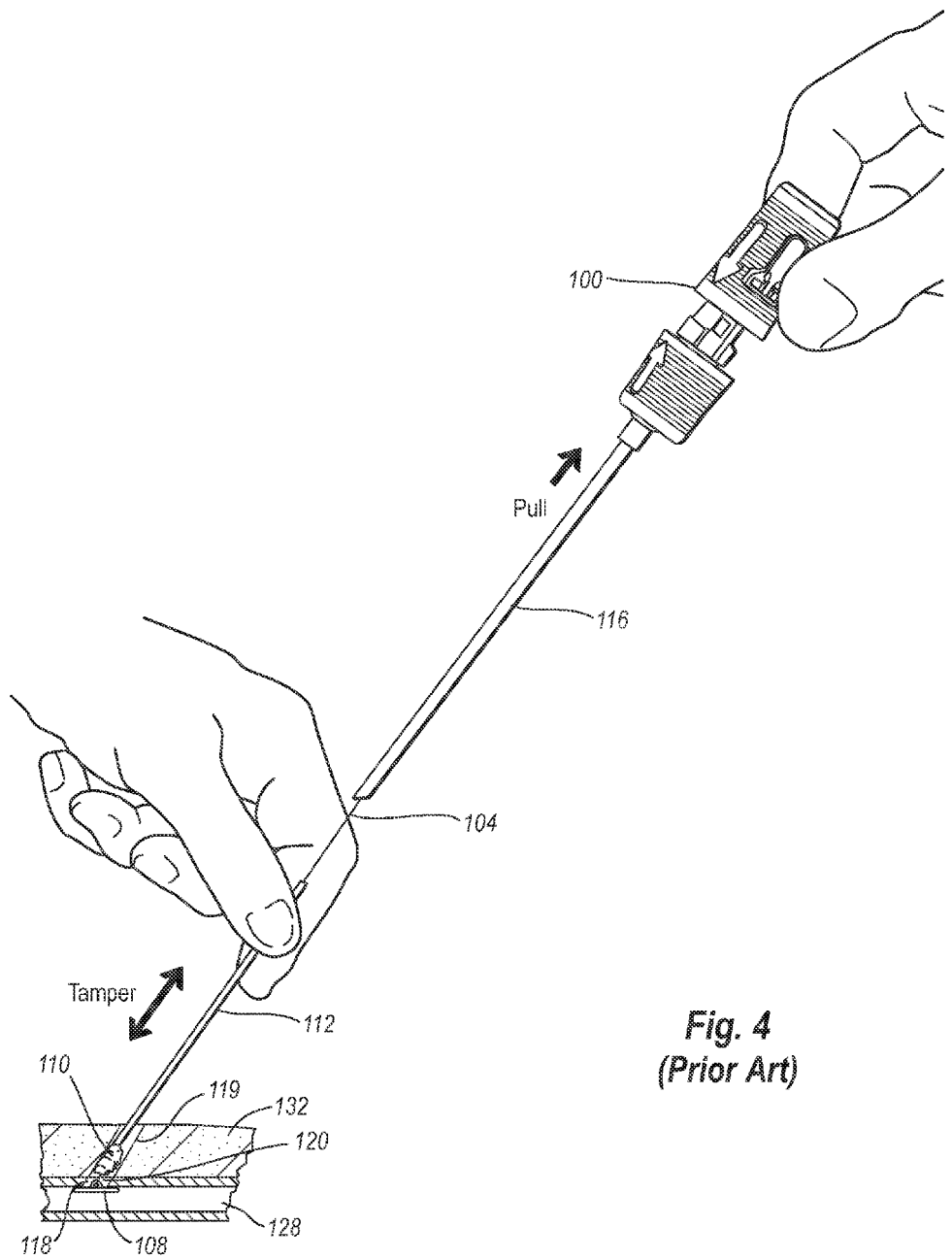
FIG. 4 is a side view of the vascular closure assembly of FIG. 1 with the operator manually compacting the sealing pad.

The flush arrangement of the anchor 108 and carrier tube 102 allows the anchor 108 to be inserted into a sheath such as insertion sheath 116 as shown in FIGS. 2-4, and eventually through an arterial puncture 118. The insertion sheath 116 is shown in FIGS. 2-4 inserted through a percutaneous incision 119 and into an artery 128. The bypass tube 114 (see FIG. 1) includes an oversized head 120 that prevents the bypass tube 114 from passing through an internal passage of the insertion sheath 116. As the vascular closure device 100 is inserted into the insertion sheath 116, the oversized head 120 bears against a surface 122 of insertion sheath 116.

Further insertion of the vascular closure device 100 results in sliding movement between the carrier tube 102 and the bypass tube 114, thereby releasing the anchor 108 from the bypass tube 114 (see FIG. 1). The anchor 108 typically remains in the flush arrangement shown in FIG. 1 following release from the bypass tube 114, limited in movement by the insertion sheath 116.

The insertion sheath 116 may include a monofold at a second or distal end 126 thereof. The monofold acts as a one-way valve to the anchor 108. A monofold is typically a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

The insertion sheath 116 may include a pair of closure device connection apertures (not shown) and a carrier tube aperture (not shown) at a proximal end 122 (see FIG. 1). The carrier tube 102 is inserted into the carrier tube aperture and the sheath connection members 130 are inserted into and releasably engage with the closure device connection apertures when assembling the vascular closure device 100 with the insertion sheath 116.

Referring next to FIGS. 3-4, with the anchor 108 deployed, the vascular closure device 100 and the insertion sheath 116 are withdrawn together, ejecting the collagen pad 110 from the carrier tube 102 into the incision tract 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 102. The tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

It may be difficult to eject and compact the collagen pad 110 using the typical tissue vascular closure device 100 described above. The insertion sheath 116 resists deformation as the collagen pad 110 is ejected from the carrier tube and compaction does not commence until the sheath 116 has been removed so as to expose the compaction member 112 for manual grasping. Under certain conditions, removal of the sheath 116 prior to compacting the collagen pad 110 causes the collagen pad 110 to retract or displace proximally from the tissue puncture 118, creating an undesirable gap between the collagen pad 110 and the puncture 118.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 5:
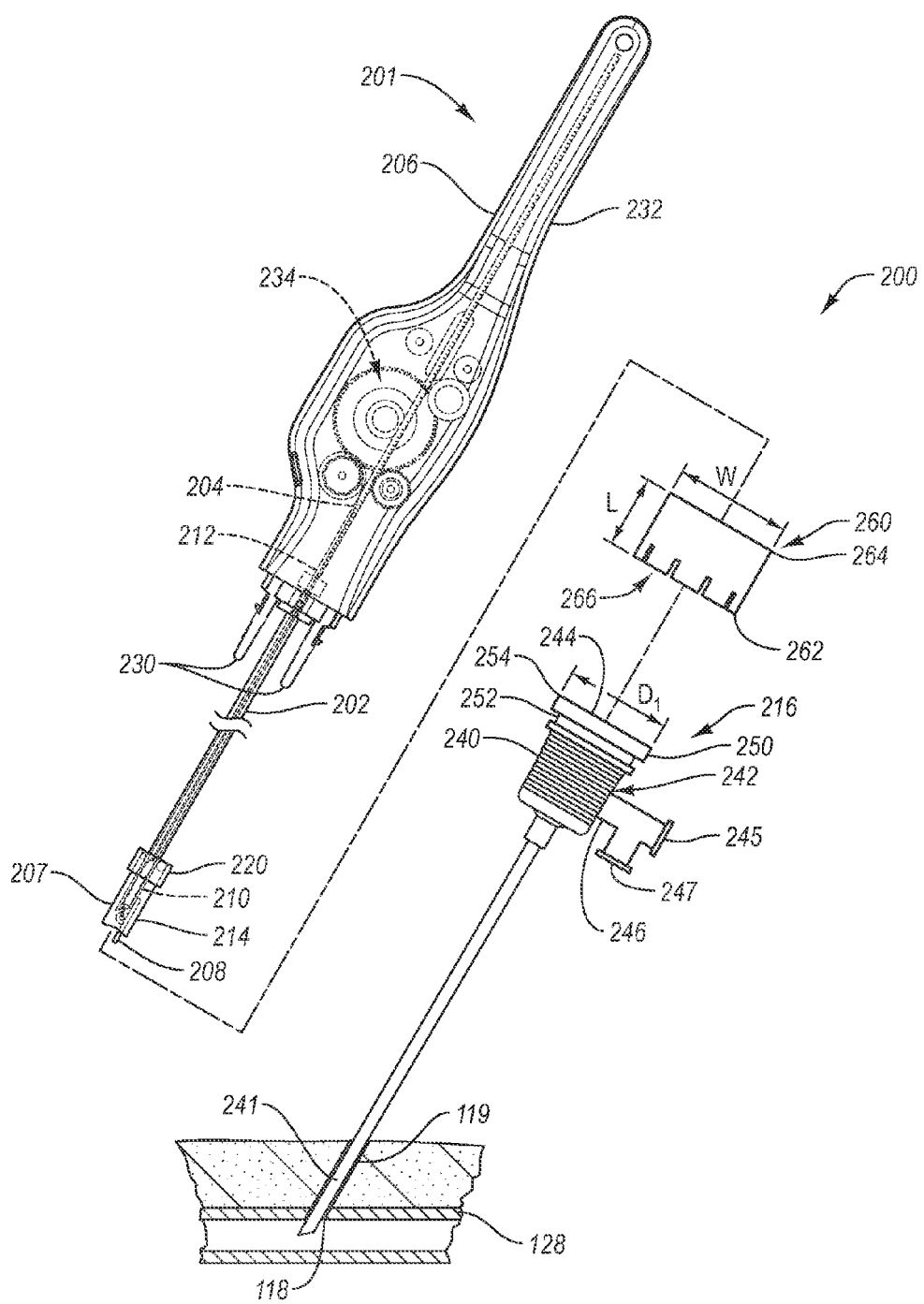
FIG. 5 is an exploded side view of another example vascular closure assembly according to the present disclosure.
Figure 6:
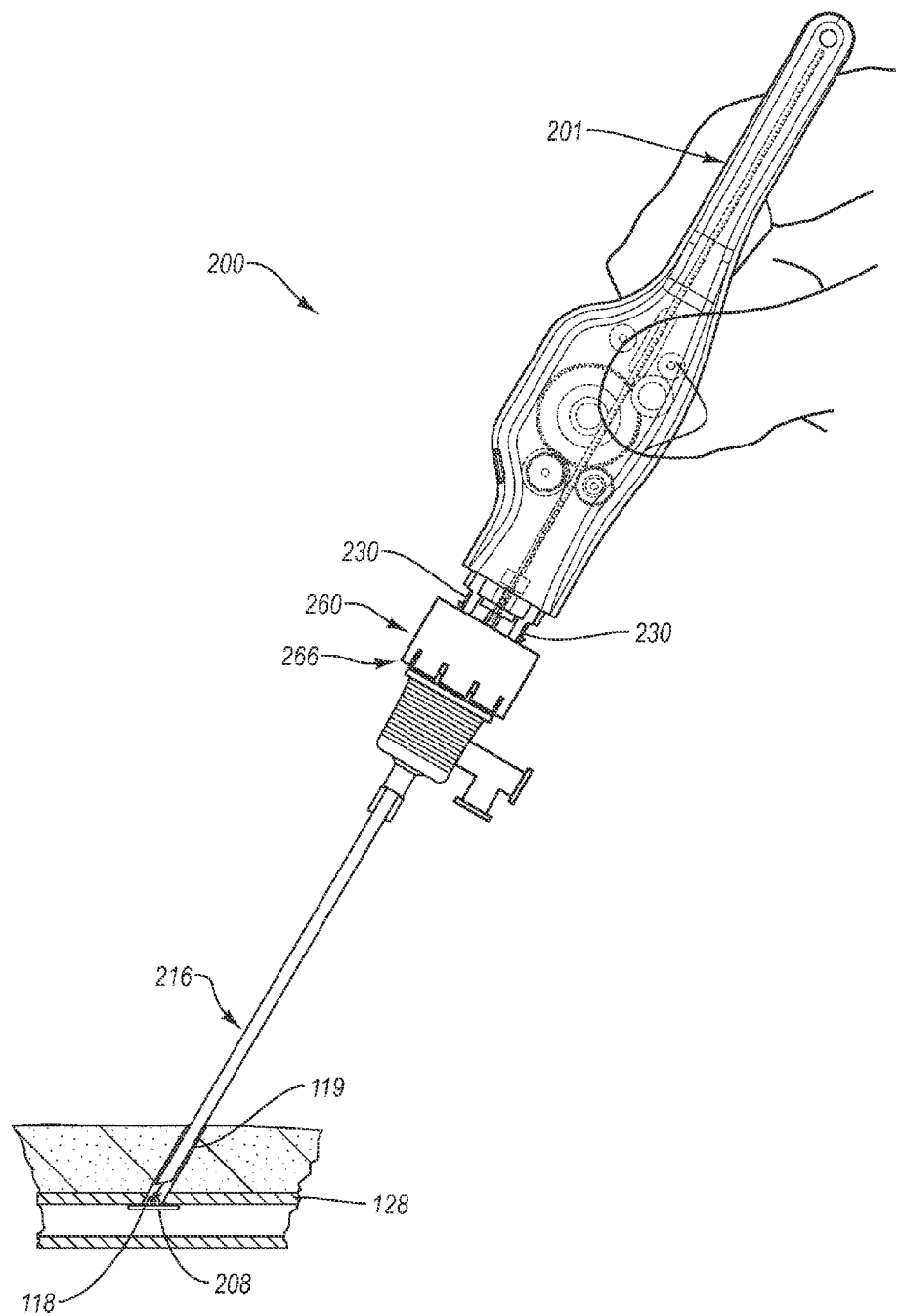
FIG. 6 is a side view of the vascular closure assembly of FIG. 5 with a portion inserted into a vascular puncture.

Referring now to FIGS. 5-9, an example vascular closure assembly 200 is shown and described. The vascular closure assembly 200 includes a vascular closure device 201, an insertion sheath 216, and an adapter 260. The insertion sheath 216 is a typical procedural sheath used in conducting an internal procedure (i.e., a treatment or diagnostics procedure conducted through a vessel of the patient) in a patient. FIGS. 5 and 6 illustrate the insertion sheath 216 partially inserted into a patient through, for example, an arterial puncture 118 of a vessel 128 and an associated percutaneous incision 119.

The vascular closure device 201 includes a carrier tube 202, a filament 204, proximal and distal ends 206, 207, an anchor 208, a pad 210, a compaction member 212, and a bypass tube 214. The bypass tube 214 may include an oversized head 220. Prior to inserting the vascular closure device 201 into the sheath 216, the anchor 208 and pad 210 are positioned within the bypass tube 214. The filament 204 is connected to the anchor 208 and pad 210 at a distal end of the filament 204. A proximal end of the filament 204 extends proximally into a handle portion 232 where it is collected by a portion of an automatic compaction assembly 234. In operation, the compaction assembly 234 drives the compaction member 212 in a distal direction to compress the pad 210 against the anchor 208 to seal the arterial puncture 118.

The vascular closure device 201 further includes at least one sheath connection member 230 that extends from the handle portion 232 in a distal direction. The sheath connection members 230 are typically arranged and configured to connect the vascular closure device 201 to an insertion sheath. In the embodiment of FIGS. 5-9, the insertion sheath 216 does not include features (e.g., apertures (not shown)) that would permit connection of the vascular closure device 201 to the insertion sheath 116 using the sheath connection members 230.

The insertion sheath 216 includes proximal and distal end portions 240, 241, and a hub assembly 242 positioned at the proximal end portion 240. The hub assembly 242 includes first and second ports, 244, 246. The second port 246 may include structure that defines first and second openings 245, 247. In some arrangements, the second port 246 is used for flushing or injecting fluids through the insertion sheath 116 and into the patient. The hub assembly 242 may also include a valve (not shown) such as a haemostatic valve arranged between at least one of the first and second ports 244, 246 and the distal end portion 241.

The hub assembly 242 may include a peripheral surface 250, a connection recess 252 defined in the peripheral surface 250, and a connection lip or edge 254. The peripheral surface 250 has a maximum outer diameter $D_1$. The outer diameter $D_1$ may define a maximum width dimension of the hub assembly 242 at the proximal end portion 240.

The adapter 260 adapts the features of insertion sheath 216 to the connection features of vascular closure device 201 to provide a connection between the insertion sheath 216 and the vascular closure device 201. The adapter 260 includes distal and proximal ends 262, 264, a sheath attachment portion 266 positioned at the distal end 262, and a plurality of apertures 268A, 268B, 270 at the distal end 262 for connection to the vascular closure device 201.

FIG. 6 illustrates the adapter 260 connected to both the insertion sheath 216 and the vascular closure device 201. The sheath attachment portion 266 may be connected to the hub assembly 242 with a snap-fit connection. The sheath connection members 230 are inserted into the closure device locking apertures 268A, 268B (shown in further detail in FIGS. 7 and 8) to provide a connection between the vascular closure device 201 and the adapter 260. In at least one configuration, the adapter 260 is releasably connected to at least one of the vascular closure device 201 and insertion sheath 216. In at least some arrangements, the adapter 260 is first connected to the insertion sheath 216 followed by insertion of at least a carrier tube 202 and sheath connection members 230 of the vascular closure device 201 into the adapter 260.

Typically, assembling the vascular closure assembly 200 as shown in FIG. 6 provides advancement of the anchor 208 through the arterial puncture 118 and percutaneous incision 119 and into the vessel 128. With the anchor 208 positioned in the vessel 128 as shown in FIG. 6, the vascular closure assembly 200 may be withdrawn proximally until the anchor contacts against an inner surface of the vessel 128 adjacent to the arterial puncture 118. Further withdrawal of the vascular closure assembly 200 results in disposal of the pad 210 adjacent to the arterial puncture 118 on an outer surface of the vessel 128 and compression of the pad 210 by the compaction member 212. Further details concerning the operation of vascular closure device 201 after positioning of the anchor 208 in the vessel 128 is described in, for example, U.S. Pat. No. 7,250,057, which patent is incorporated in its entirety herein by reference.

Figure 7:
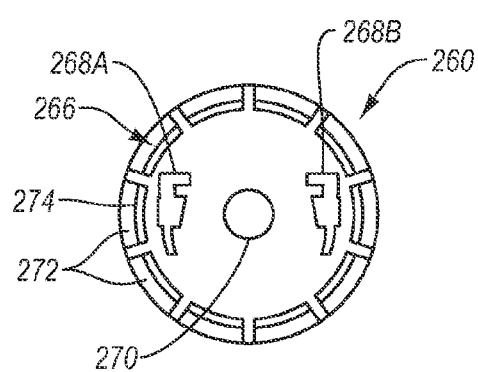
FIG. 7 is a first end view of the adapter of the vascular closure assembly of FIG. 5.
Figure 8:
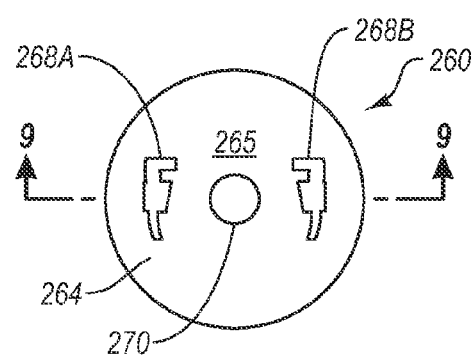
FIG. 8 is an opposite end view of the adapter of FIG. 7.
Figure 9:
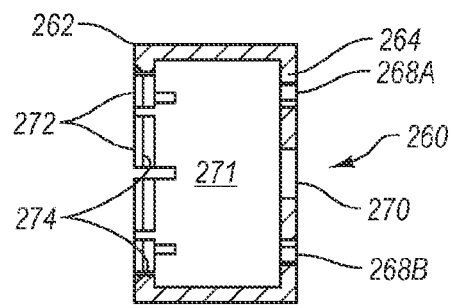
FIG. 9 is a cross-sectional view of the adapter of FIG. 7.
Figure 10:
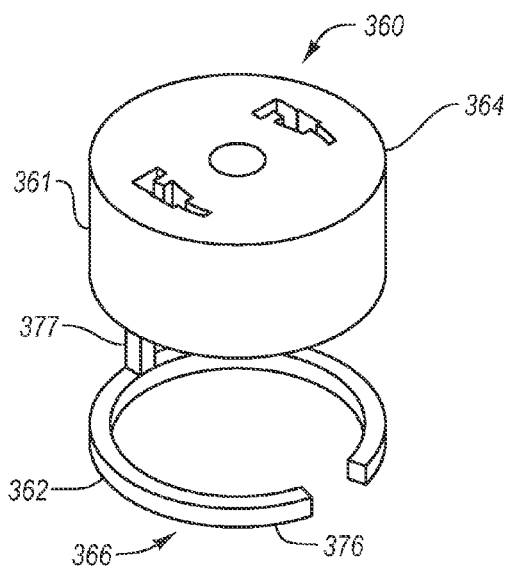
FIG. 10 is a perspective view of another example adapter for use with the vascular closure assembly of FIG. 5.
Figure 11:
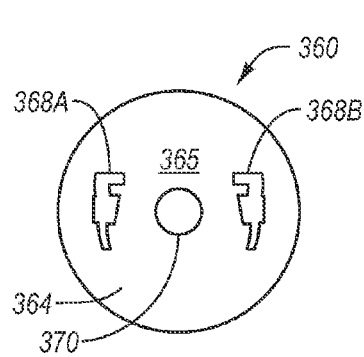
FIG. 11 is a first end view of the adapter of FIG. 10.
Figure 12:
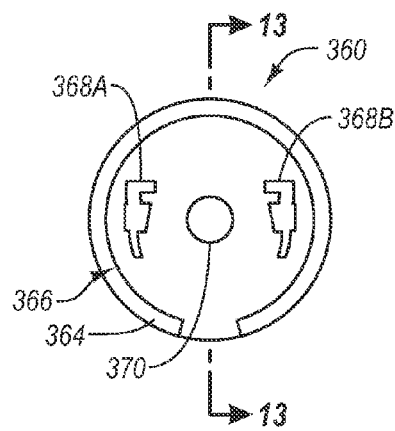
FIG. 12 is an opposite end view of the adapter of FIG. 10.
Figure 13:
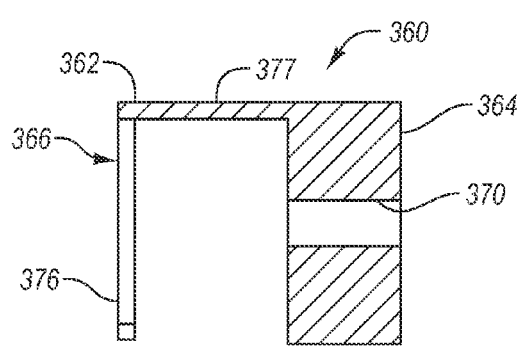
FIG. 13 is a cross-sectional view of the adapter of FIG. 10.
Figure 14:
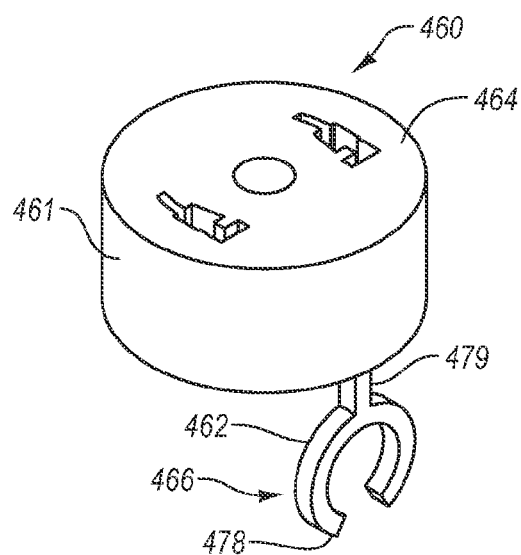
FIG. 14 is a perspective view of another example adapter for use with the vascular closure assembly of FIG. 5.
Figure 15:
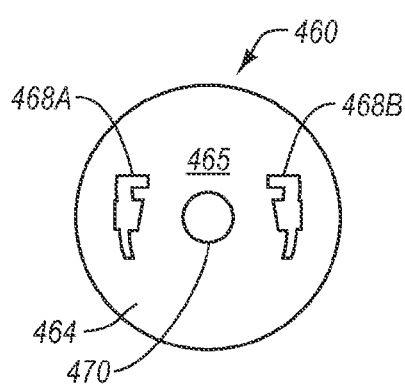
FIG. 15 is a first end view of the adapter of FIG. 14.
Figure 16:
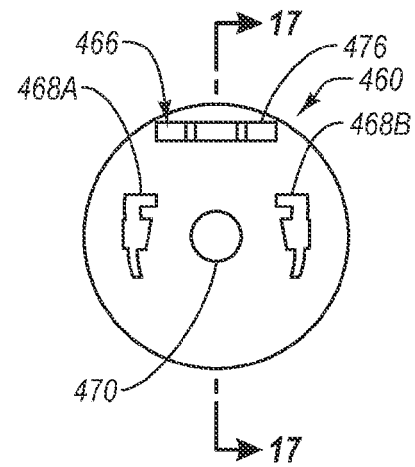
FIG. 16 is an opposite end view of the adapter of FIG. 14.
Figure 17:
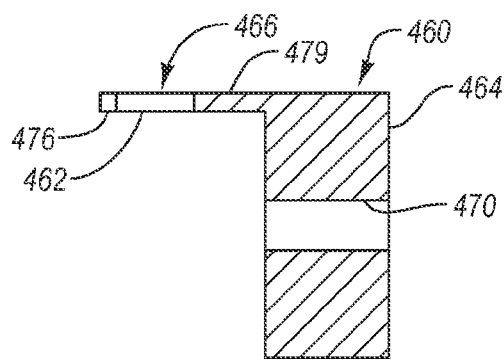
FIG. 17 is a cross-sectional view of the adapter of FIG. 14.
Figure 18:
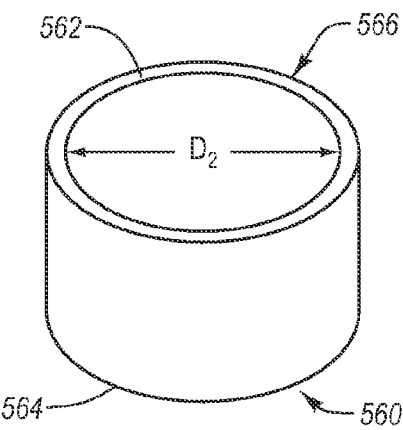
FIG. 18 is a perspective view of another example adapter for use with the vascular closure assembly of FIG. 5.
Figure 19:
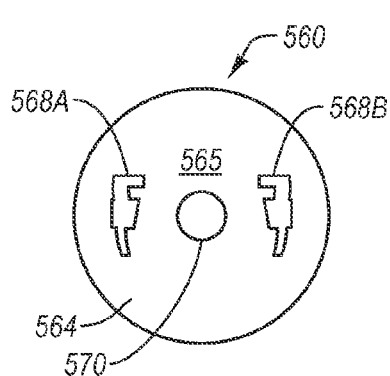
FIG. 19 is a first end view of the adapter of FIG. 18.
Figure 20:
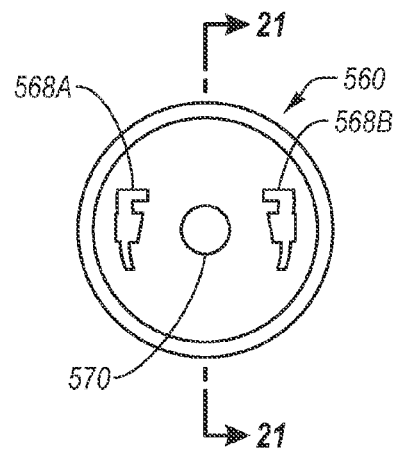
FIG. 20 is an opposite end view of the adapter of FIG. 18.
Figure 21:
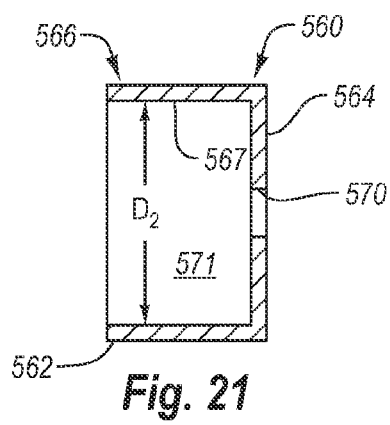
FIG. 21 is a cross-sectional view of the adapter of FIG. 18.
Figure 22:
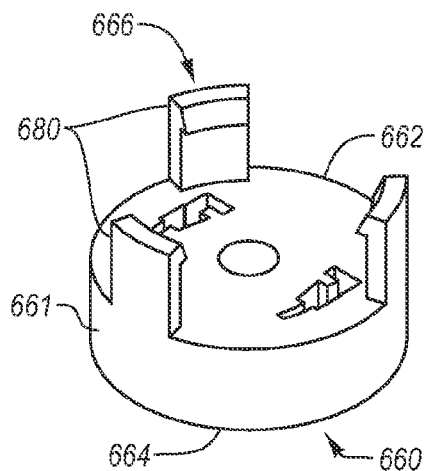
FIG. 22 is a perspective view of another example adapter for use with the vascular closure assembly of FIG. 5.
Figure 23:
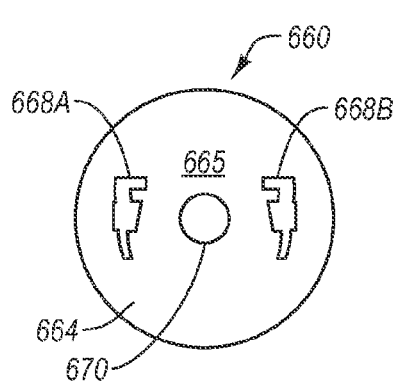
FIG. 23 is a first end view of the adapter of FIG. 22.
Figure 24:
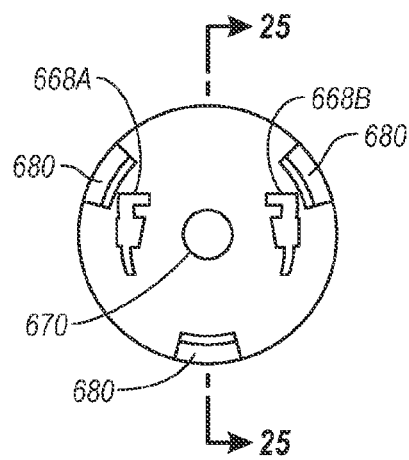
FIG. 24 is an opposite end view of the adapter of FIG. 22.
Figure 25:
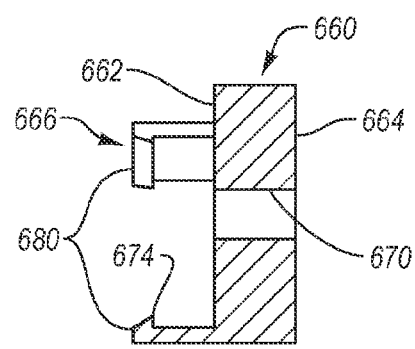
FIG. 25 is a cross-sectional view of the adapter of FIG. 22.
Figure 26:
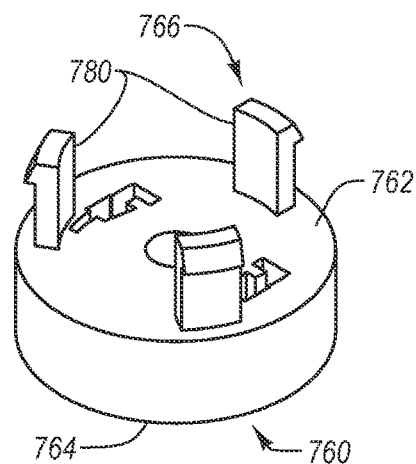
FIG. 26 is a perspective view of another example adapter for use with the vascular closure assembly of FIG. 5.
Figure 27:
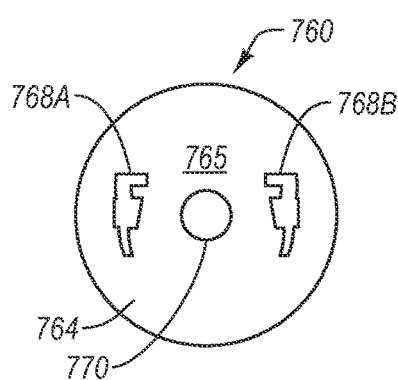
FIG. 27 is a first end view of the adapter of FIG. 26.
Figure 28:
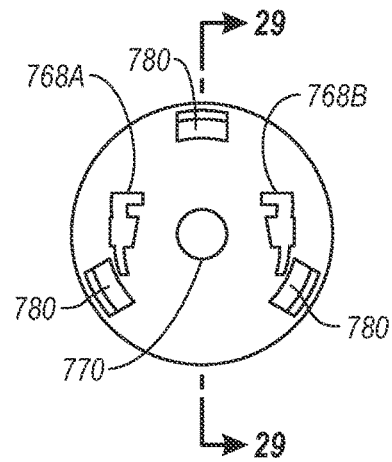
FIG. 28 is an opposite end view of the adapter of FIG. 26.
Figure 29:
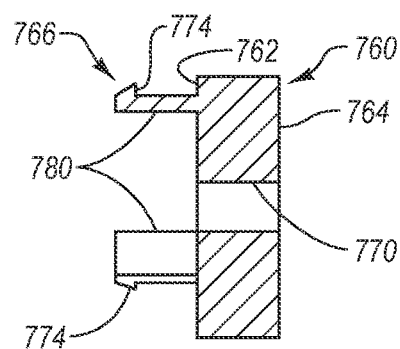
FIG. 29 is a cross-sectional view of the adapter of FIG. 26.
Figure 30:
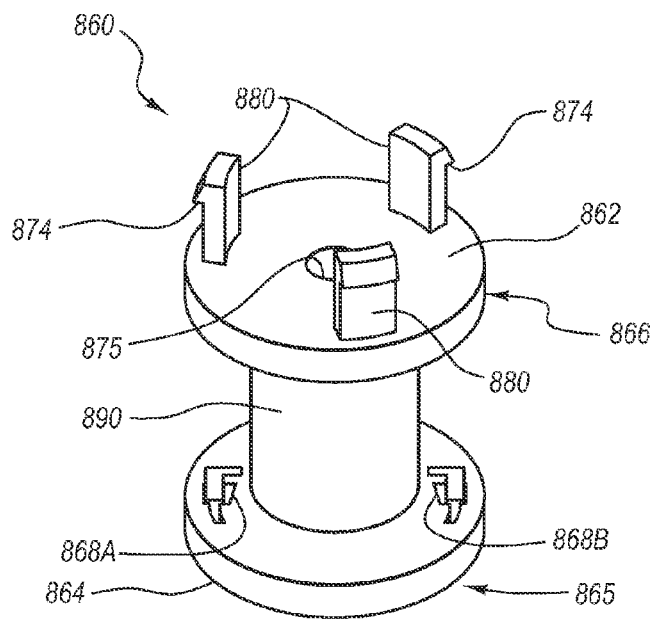
FIG. 30 is a perspective view of another example adapter for use with the vascular closure assembly of FIG. 5.
Figure 31:
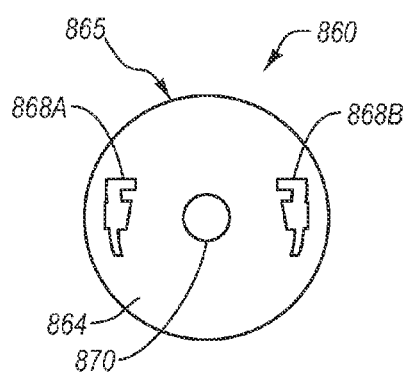
FIG. 31 is a first end view of the adapter of FIG. 30.
Figure 32:
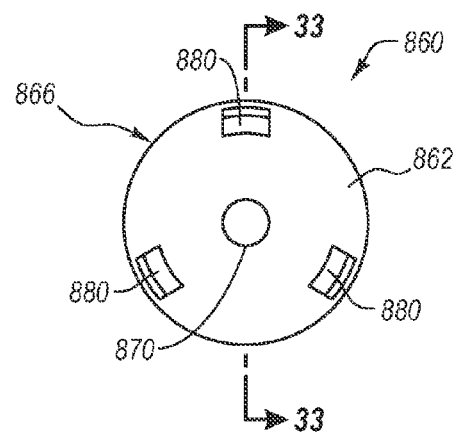
FIG. 32 is an opposite end view of the adapter of FIG. 30.

Referring to FIGS. 7-9, the sheath attachment portion 266 of the adapter 260 includes a plurality of latching arms 272. The latching arms 272 may include a latching surface 274. The latching arms 272 may be flexible radially outward to permit insertion of the first port 244 of the hub assembly 242 into an interior 271 of adapter 260. The latching surface 274 may move radially inward into the connection recess 252 to provide a snap-fit connection between the adapter 260 and the insertion sheath 216.

The closure device locking apertures 268A, 268B and the carrier tube aperture 270 are defined in the adapter 260 on the rear surface 265 at the proximal end 264. The locking apertures 268A, 268B are sized to receive the sheath connection members 230. In at least one arrangement, the sheath connection members 230 engage the locking apertures 268A, 268B in a releasable snap-fit connection. The carrier tube 202 is inserted into the insertion sheath 216 through the carrier tube aperture 270. As shown in FIGS. 7-8, the locking apertures 268A, 268B have a closed perimeter within the proximal end 264. Additional closed-perimeter locking apertures are shown in FIGS. 10-12, 14-16, 19-20, 22-24, 26-28, and 30-32.

Referring to FIG. 5, in at least one example, the adapter 260 has a length in the axial direction in the range of about 3 to about 25 millimeters, and a width in the range of about 10 to about 40 millimeters. The dimensions L and W may depend, at least partially upon the French size of the carrier tube of the vascular closure device and the French size of the insertion portion of the insertion sheath.

FIGS. 10-13 illustrate another example adapter 360 constructed for use with the insertion sheath 216 and vascular closure device 201 described above. The adapter 360 includes distal and proximal ends 362, 364, and a sheath attachment portion 366 extending from the distal end 362. A pair of closure device locking apertures 368A, 368B and a carrier tube aperture 370 are defined in a rear surface 365 at the proximal end 364.

The sheath attachment portion 366 includes an annular ring 376 spaced distally from a base portion 361 of the adapter 360 with an extension arm 377. The annular ring 376 is arranged and configured to fit into the connection recess 252 of the insertion sheath 216. The annular ring 376 may be inserted into the connection recess 252 from a lateral or side direction (i.e., a direction generally perpendicular to a direction of insertion of the insertion sheath 216 into the arterial puncture 118).

In some arrangements, multiple extension arms 377 are used to connect the annular ring 376 to the base portion 361. In at least one arrangement, the annular ring 376 is continuous and comprises a flexible, resilient material that permits expansion of the annular ring 376 over the connection lip 254 and into the connection recess 252.

The locking apertures 368A, 368B are sized to receive the sheath connection members 230 of the closure device 201. In at least one arrangement, the sheath connection members 230 engage the locking apertures 368A, 368B in a releasable snap-fit connection. The carrier tube 202 is inserted into the insertion sheath 216 through the carrier tube aperture 370.

FIGS. 14-17 illustrate another example adapter 460. The adapter 460 includes distal and proximal ends 462, 464, a sheath attachment portion 466 extending from the distal end 462, and apertures 468A, 468B, 470 defined in a rear surface 465 at the proximal end 464. The sheath attachment portion 466 extends distally from a base portion 461 of the adapter 460.

The sheath attachment portion 466 includes an annular ring 478 that is arranged generally parallel with the direction of insertion of the insertion sheath 116. The annular ring 478 includes an opening along a distal facing end that permits connection of the annular ring 478 to the second part 246 of the hub assembly 248. The annular ring 478 is spaced distally from the base portion 461 with an extension arm 477.

The annular rings 376 and 476 may be configured to releasably mount to the hub assembly 242. In some arrangements, the annular rings 376, 478 may provide a permanent connection to the hub assembly 242. In other arrangements, the annular rings 376, 478 may be used in combination with other sheath attachment constructions described herein.

The locking apertures 468A, 468B are sized to receive the sheath connection members 230 of the closure device 201. In at least one arrangement, the sheath connection members 230 engage the locking apertures 468A, 468B in a releasable snap-fit connection. The carrier tube 202 is inserted into the insertion sheath 216 through the carrier tube aperture 470.

Referring to FIGS. 18-21, another example adapter 560 is shown and described. The adapter 560 includes distal and proximal ends 562, 564, a sheath attachment portion 566 at the distal end 562, and apertures 568A, 568B, 570 defined in a rear surface 565 at the proximal end 564. The adapter 560 defines the adapter interior or recess 571 having an internal dimension $D_2$. Typically, the recess 571 is sized to receive the hub assembly 242 such that an interference fit occurs between the peripheral surface 250 of the hub assembly 242 and an inner surface 567 of the sheath attachment portion 566. In some arrangements, the inner surface 567 includes a taper so that the dimension $D_2$ is greater than the dimension $D_1$ along at least a portion of the inner surface 567 for easier insertion of the hub assembly 242 into the adapter 560, and the dimension $D_2$ is equal to or less than the dimension $D_1$ along another portion of the inner surface 567 to provide the interference fit described above.

The adapter 560 may be particularly useful with insertion sheaths that do not include a connection recess adjacent to the first port 244. In some arrangements, the interference fit type sheath attachment portion 566 may be used in combination with other connection features such as the annular rings 478 described above.

The locking apertures 568A, 568B are sized to receive the sheath connection members 230 of the closure device 201. In at least one arrangement, the sheath connection members 230 engage the locking apertures 568A, 568B in a releasable snap-fit connection. The carrier tube 202 is inserted into the insertion sheath 216 through the carrier tube aperture 570.

Referring now to FIGS. 22-25, another example adapter 660 is illustrated and described. The adapter 660 includes distal and proximal ends 662, 664, a sheath attachment portion 666 extending from the distal end 662, and a plurality of apertures 668A, 668B, 670 defined in a rear surface 665 at the proximal end 664.

The sheath attachment portion 666 may include a plurality of clip members 680 that extend distally from a base portion 661. The clip members 680 may include latching portions 674 facing generally radially inward. The latching portion 674 may be configured to contact an outer periphery surface 252 of the insertion sheath 216, or may be configured to contact within the connection recess 252.

In at least one example, the clip members 680 are flexible radially outward to permit movement around the connection lip 254 and along the peripheral surface 250 of the insertion sheath 216. The clip members 680 are able to move distally along the peripheral surface 250 and then contact the peripheral surface 250 when attempted to move in the proximal direction, thereby limiting separation of the anchor 260 from the insertion sheath 216 in the axial direction. In at least one example, the latching portions 674 are configured as barbs or similar structures that penetrate into the peripheral surface 250 to provide the desired connection.

The locking apertures 668A, 668B are sized to receive the sheath connection members 230 of the closure device 201. In at least one arrangement, the sheath connection members 230 engage the locking apertures 668A, 668B in a releasable snap-fit connection. The carrier tube 202 is inserted into the insertion sheath 216 through the carrier tube aperture 670.

FIGS. 26-29 illustrate another adapter 760 that includes distal and proximal ends 762, 764, a sheath attachment portion 766 extending from the distal end 762, and a plurality of apertures 768A, 768B, 770 defined in a rear surface 765 at the proximal end 764. The sheath attachment portion 766 includes a plurality of clip members 780 extending from the base portion 761 of the adapter 760. The clip members 780 include a latching portion 774 that faces generally radially outward (see FIG. 29). Typically, the clip members 780 are arranged to permit insertion of the clip members 780 into an inner cavity (not shown) of the first port 244. The latching portion 774 may contact an inner surface of the inner cavity of the first port 244 to limit separation of the adapter 760 from the insertion sheath 216.

The locking apertures 768A, 768B are sized to receive the sheath connection members 230 of the closure device 201. In at least one arrangement, the sheath connection members 230 engage the locking apertures 768A, 768B in a releasable snap-fit connection. The carrier tube 202 is inserted into the insertion sheath 216 through the carrier tube aperture 770.

FIGS. 30-33 illustrate another adapter 860 that includes distal and proximal ends 862, 864, a sheath attachment portion 866 positioned at the distal end 862, a plurality of apertures 868A, 868B defined in an adapter portion 865, and a carrier tube aperture 870 extending from the proximal end 862 to the distal end 864. An extension member 890 extends between the sheath attachment portion 866 and the adapter portion 865.

The sheath attachment portion 866 includes a plurality of clip members 880 extending distally. The clip members 880 include a latching portion 874 that faces generally radially outward. Typically, the clip members 880 are arranged to permit insertion of the clip members 880 into an inner cavity (not shown) of the first port 244. The latching portion 874 may contact an inner surface of the inner cavity of the first port 244 to limit separation of the adapter 860 from the insertion sheath 216.

The locking apertures 868A, 868B are sized to receive the sheath connection members 230 of the closure device 201. In at least one arrangement, the sheath connection members 230 engage the locking apertures 868A, 868B in a releasable snap-fit connection. The carrier tube 202 is inserted into the insertion sheath 216 through the carrier tube aperture 870.

Figure 33:
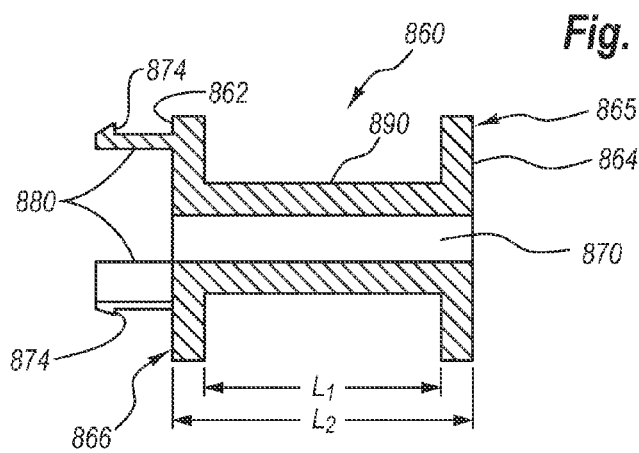
FIG. 33 is a cross-sectional view of the adapter of FIG. 30.

The extension portion 890 may have various lengths $L_1$ that influence a total length $L_2$ of the adapter 860 (see FIG. 33). The extension portion 890 may have an adjustable length. Different length adapters 860 may have extension portions 890 having different lengths $L_1$. Adapters 860 of various lengths or adjustable lengths may be used to account for different length insertion sheaths 216.

The adapters described above with reference to the attached figures are configured for attachment to the insertion sheath by moving the adapter linearly in an axial direction (i.e., in the direction of insertion of the insertion sheath with the insertion sheath into the arterial puncture). Other types of sheath attachment portion constructions are possible that require different or additional types of relative motion between the adapter and the insertion sheath. For example, the sheath attachment portion may be constructed to require some rotational movement of the adapter relative to the insertion sheath. In at least one example, the sheath attachment portion includes a twist lock type design wherein at least some rotational motion is needed to provide attachment between the adapter and the insertion sheath.

The example vascular closure devices described above include a pair of sheath connection members that may provide a releasable connection between the vascular closure device and the adapter. Other connection features are possible in place of or in combination with the sheath connection members. For example, a single sheath connection member may be used. In other example, a connection feature extends around and contacts an outer surface of the adapter or insertion sheath may be used. In a still further example, the connection structure provides a permanent connection between the vascular closure device and the adapter or insertion sheath.

Generally, the adapter provides a connection interface between any type of vascular closure device and its associated features for connection to an insertion sheath, and an insertion sheath of any particular construction. The adapter typically provides a connection interface between a vascular closure device and an insertion sheath. In at least some embodiments, the adapter provides a releasable connection to at least one of the vascular closure device and insertion sheath.

The adapters described herein may comprise a single material or a plurality of materials. For example, at least portions of the adapter may comprise a polymeric material such as polypropylene. In other arrangements, a portion of the adapter may comprise a metal material such as stainless steel, tungsten, or Nitinol. The adapter may be formed using a variety of methods including, for example, injection molding, co-molding, and casting.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A sheath adapter configured for use between a tissue puncture closure device and a procedural sheath, the procedural sheath adapted for insertion into a tissue puncture, and the tissue puncture closure device adapted for partial insertion into the procedural sheath and sealing of the tissue puncture, the sheath adapter comprising:
   a sheath connection portion positioned at a distal end of the sheath adapter, the sheath connection portion including at least one latch member configured to releasably mount the sheath adapter to the procedural sheath by extending into a recess of the procedural sheath;
   a closure device connection portion of the body positioned at a proximal end of the sheath adapter, the distal end and the proximal end being opposite ends of the sheath adapter with respect to a central axis of the adapter, said central axis extending between the distal end and the proximal end, the proximal end defining a proximal end wall which faces a direction along the central axis away from the distal end, said proximal end wall, as viewed in a cross-section taken along the central axis, extending perpendicular to the central axis;
   the closure device connection portion having at least one connection aperture opening on the proximal end wall and sized to releasably mount the sheath adapter to the tissue closure device by receiving a sheath connection member of the tissue closure device, the at least one connection aperture having a closed perimeter within the closure device connection portion and being disposed radially inward, with respect to the central axis, of the at least one latch member;
   an open aperture opening on the proximal end wall and configured to receive passage of a carrier tube of the tissue puncture closure device through the sheath adapter.

2. The sheath adapter of claim 1, wherein the sheath connection portion is configured to provide an interference fit with an outer surface of the procedural sheath.

3. The sheath adapter of claim 1, wherein the sheath connection portion is configured to releasably mount to a proximal end portion of the procedural sheath, and the closure device connection portion is configured to releasably mount to a sheath connection member of the tissue puncture closure device.

4. The sheath adapter of claim 1, wherein the sheath adapter is configured to receive a plurality of different sheaths of different lengths.

* * * * *